United States Patent
Koerner et al.

(10) Patent No.: US 7,285,108 B2
(45) Date of Patent: Oct. 23, 2007

(54) ACTIVE SYSTEM FOR DEFLECTING A DISTAL PORTION OF A CATHETER INTO A HOOP CONFIGURATION

(75) Inventors: Richard J. Koerner, San Diego, CA (US); David J. Lentz, La Jolla, CA (US); Joseph A. O'Donnell, Escondido, CA (US); Alvin B. Salinas, San Marcos, CA (US)

(73) Assignee: Cryocor, Inc., San Diego, CA (US)

( * ) Notice: Subject to any disclaimer, the term of this patent is extended or adjusted under 35 U.S.C. 154(b) by 205 days.

(21) Appl. No.: 10/876,312

(22) Filed: Jun. 24, 2004

(65) Prior Publication Data

US 2005/0288626 A1 Dec. 29, 2005

(51) Int. Cl.
*A61M 31/00* (2006.01)
*A61B 1/00* (2006.01)

(52) U.S. Cl. .................... 604/95.04; 600/146
(58) Field of Classification Search ............ 604/93.01, 604/95.04; 600/129, 145–147, 149
See application file for complete search history.

(56) References Cited

U.S. PATENT DOCUMENTS

| 1,060,665 | A | 5/1913 | Bell |
|---|---|---|---|
| 2,574,840 | A | 11/1951 | Pieri et al. |
| 2,688,329 | A | 9/1954 | Wallace |
| 3,605,725 | A | 9/1971 | Bentov |
| 4,245,624 | A | 1/1981 | Komiya |
| 4,456,017 | A | 6/1984 | Miles |
| 4,586,923 | A | 5/1986 | Gould et al. |
| 4,813,434 | A | 3/1989 | Buchbinder et al. |
| 4,815,478 | A | 3/1989 | Buchbinder et al. |
| 4,886,067 | A | 12/1989 | Palermo |
| 4,960,134 | A | 10/1990 | Webster, Jr. |
| 4,960,411 | A | 10/1990 | Buchbinder |
| 4,976,688 | A | 12/1990 | Rosenblum |
| 5,037,391 | A | 8/1991 | Hammerslag et al. |
| 5,042,985 | A | 8/1991 | Elliott et al. |
| 5,108,368 | A | 4/1992 | Hammerslag et al. |
| 5,114,414 | A | 5/1992 | Buchbinder |
| 5,125,895 | A | 6/1992 | Buchbinder et al. |
| 5,190,050 | A | 3/1993 | Nitzsche |
| 5,242,441 | A | 9/1993 | Avitall |

(Continued)

FOREIGN PATENT DOCUMENTS

EP 0790066 A2 8/1997

*Primary Examiner*—LoAn H Thanh
(74) *Attorney, Agent, or Firm*—Nydegger & Associates

(57) ABSTRACT

An active system for deflecting a distal portion of a catheter into a hoop configuration includes an elongated catheter body having a proximal portion and a distal portion that is formed with a lumen. A thin-walled tube, which is typically made of a metallic material, is positioned in the lumen. The tube includes a cylindrical wall and includes a plurality of lateral slits that are typically formed in the tube wall and arranged such that the tube can be transformed between a relaxed, cylindrical configuration and a deflected configuration wherein the tube is substantially hoop shaped. One end of a deflection wire is attached to the tube and the other wire end is attached to a reel that is rotationally mounted onto a catheter handle housing. In use, the reel is rotated to axially retract the wire and transform the tube into a hoop configuration.

15 Claims, 6 Drawing Sheets

U.S. PATENT DOCUMENTS

| | | |
|---|---|---|
| 5,299,562 A | 4/1994 | Heckele et al. |
| 5,318,525 A | 6/1994 | West et al. |
| 5,322,064 A | 6/1994 | Lundquist et al. |
| 5,330,466 A | 7/1994 | Imran |
| 5,334,145 A * | 8/1994 | Lundquist et al. ....... 604/95.04 |
| 5,368,564 A | 11/1994 | Savage |
| 5,507,725 A | 4/1996 | Savage et al. |
| 5,656,030 A | 8/1997 | Hunjan et al. |
| 5,715,817 A | 2/1998 | Stevens-Wright et al. |
| 5,891,088 A | 4/1999 | Thompson et al. |
| 5,906,590 A | 5/1999 | Hunjan et al. |
| 5,928,191 A | 7/1999 | Houser et al. |
| 5,944,689 A | 8/1999 | Houser et al. |
| 6,013,052 A | 1/2000 | Durman et al. |
| 6,066,125 A | 5/2000 | Webster, Jr. |
| 6,106,518 A | 8/2000 | Wittenberger et al. |
| 6,123,699 A | 9/2000 | Webster, Jr. |
| 6,171,277 B1 | 1/2001 | Ponzi |
| 6,183,435 B1 | 2/2001 | Bumbalough et al. |
| 6,183,463 B1 | 2/2001 | Webster, Jr. |
| 6,198,974 B1 | 3/2001 | Webster, Jr. |
| 6,210,407 B1 | 4/2001 | Webster |
| 6,254,568 B1 | 7/2001 | Ponzi |
| 6,267,746 B1 | 7/2001 | Bumbalough |
| 6,319,248 B1 | 11/2001 | Nahon |
| 6,332,880 B1 | 12/2001 | Yang et al. |
| 6,346,099 B1 | 2/2002 | Altman |
| 6,413,234 B1 | 7/2002 | Thompson et al. |
| 6,440,126 B1 | 8/2002 | Abboud et al. |
| 6,468,260 B1 | 10/2002 | Bumbalough et al. |
| 6,485,455 B1 | 11/2002 | Thompson et al. |
| 6,500,167 B1 * | 12/2002 | Webster, Jr. ................ 604/528 |
| 6,522,933 B2 | 2/2003 | Nguyen |
| 6,540,725 B1 | 4/2003 | Ponzi |
| 6,551,271 B2 | 4/2003 | Nguyen |
| 6,569,114 B2 | 5/2003 | Ponzi et al. |
| 6,571,131 B1 | 5/2003 | Nguyen |
| 6,579,278 B1 | 6/2003 | Bencini |
| 6,585,717 B1 * | 7/2003 | Wittenberger et al. ...... 604/523 |
| 6,585,718 B2 | 7/2003 | Hayzelden et al. |
| 6,602,278 B1 | 8/2003 | Thompson et al. |
| 6,605,086 B2 | 8/2003 | Hayzelden et al. |
| 6,607,505 B1 | 8/2003 | Thompson et al. |
| 6,610,058 B2 | 8/2003 | Flores |
| 2001/0025075 A1 | 9/2001 | Smith et al. |
| 2002/0025998 A1 | 2/2002 | McCullough et al. |

* cited by examiner

ACTIVE SYSTEM FOR DEFLECTING A DISTAL PORTION OF A CATHETER INTO A HOOP CONFIGURATION

FIELD OF THE INVENTION

The present invention pertains generally to systems and methods for deflecting a distal portion of a catheter while the distal portion is positioned within a body conduit. More particularly, the present invention pertains to an active system for deflecting the distal portion of a catheter into a hoop configuration. The present invention is particularly, but not exclusively, useful as a system for actively deflecting the distal portion of a cryo-catheter into a hoop configuration.

BACKGROUND OF THE INVENTION

Atrial fibrillation is an irregular heart rhythm that adversely affects approximately 2.5 million people in the United States. It is believed that at least one-third of all atrial fibrillation originates near the ostium of the pulmonary veins. Anatomically, two pairs of pulmonary veins are connected to the left atrium of the heart with each pair delivering blood to the heart from one of the patient's lungs.

It is further believed that the optimal technique to treat atrial fibrillation is to create circumferential lesions around the ostia where a pulmonary vein connects with the left atrium. More specifically, the goal is to ablate tissue to form a conduction block to thereby prohibit the transmission of irregular electrical signals that can cause an arrhythmia. To be effective, the conduction block must completely block irregular signals and this often requires the ablation of a relatively deep, uniform lesion.

Heretofore, due to the relatively large diameters of these ostia, cryoablation procedures have typically been accomplished using multiple, successive contacts between a cryo-element and the tissue around the periphery of an ostium. More specifically, these procedures have required the cryo-element to be successively moved around the ostia to create a patchwork array of ablations. This often results in a non-uniform circumferential ablation that fails to form an adequate conduction block. Moreover, these multiple contact procedures tend to be complicated, time consuming, difficult to perform, and generally unreliable.

To simplify and quicken the procedure and produce a more uniform lesion, it is desirable to make circumferentially shaped lesions, either in a single contact or with as few contacts as possible. This, in turn, implies the use of a hoop shaped or partially hoop shaped contacting element. One approach to establishing a hoop shaped lesion is to use a so-called "passive" contacting element. In greater detail, this generally involves pre-forming a contacting element in a curved or hoop shape. The passive contacting element is then deformed into a straight configuration and passed through a guiding tube to reach the treatment site. At the site, the contacting element is emitted from the distal end of the guiding tube where it relaxes into its pre-formed shape.

Unfortunately, passive contact elements have several drawbacks. For one, it can be somewhat difficult to guide the deformed element through the tortuous vasculature, due in part to the resistance presented by the deformed contact element in the guide tube. In addition, the size (i.e. radius) of the hoop generated using a passive contact element is typically not adjustable in situ. This later drawback can be significant, for example, when more than one lesion is needed and different hoop sizes are required for each lesion.

In light of the above, it is an object of the present invention to provide systems and methods suitable for the purposes of cryoablating substantially circumferential ablations of internal tissue, while minimizing the number of tissue-cryo-element contacts. It is another object of the present invention to provide systems and methods for actively forming a hoop shaped contact element in a body conduit. It is yet another object of the present invention to provide systems and methods for cryoablating internal target tissue that can be performed quickly and are relatively reliable.

SUMMARY OF THE INVENTION

The present invention is directed to an active system for deflecting a distal portion of a catheter into a hoop configuration. Corresponding methods of preparation and use are also included. For the invention, the distal portion of the flexible catheter can be actively reconfigured inside a body conduit from a substantially straight, tubular shape to a hoop configuration in response to the proximal movement of a single deflection wire.

In greater structural detail, the system includes an elongated catheter body having a proximal portion and a distal portion that is formed with a lumen. For the system, a thin-walled tube, which is typically made of a metallic material, is positioned in the lumen of the distal portion. Specifically, the tube includes a cylindrical wall that defines a tube axis and it includes a plurality of slits that are typically formed in the tube wall by a laser cutting process.

In a particular embodiment, the tube in the distal portion of the catheter body is formed with a plurality of first slits. These first slits are cut through the tube wall, and are oriented in respective planes that are substantially perpendicular to the tube axis. Each first slit extends azimuthally in an arc partway around the axis and each slit has a center. Also, all of the first slits have a substantially same arc length. Further, the respective centers of these first slits are aligned with each other in a first centerline that is oriented substantially parallel to the tube axis. For this embodiment, the tube is also formed with a plurality of second slits. In all important respects, these second slits are like the first slits. Specifically, the second slits establish a second centerline that is also substantially parallel to the tube axis. Typically, however, the second slits are cut into the tube wall such that the second centerline is diametrically opposed to the first centerline. With this arrangement of first and second slits, the tube can be transformed between a first, relaxed configuration wherein the tube is substantially cylindrical shaped, and a second, deflected configuration wherein the tube is substantially hoop shaped.

Also for the deflecting system, the distal end of a deflection wire is attached to the distal end of the tube. The wire then extends from the distal end of the tube, and through the catheter tube to a catheter handle. In one embodiment, the catheter handle includes a handle housing and reel that is attached to the handle housing. With this attachment, the reel is allowed to rotate about an axis of rotation relative to the housing. For this embodiment, the proximal end of the deflection wire is attached to the reel at a radial distance from the axis of rotation. With this cooperation of structure, the reel can be rotated relative to the handle housing to axially retract the deflection wire and thereby transform the tube from the first configuration to the second configuration, wherein the distal portion of the catheter is reshaped into a hoop configuration.

In one implementation of the deflection system, a guiding mechanism is provided to maintain the deflection wire adjacent to the inner wall of the tube during a deflection of the tube. For example, this guiding mechanism can include a plurality of indentations that are formed in the tube to hold the deflection wire against the inner wall while allowing the deflection wire to pass freely through each indentation. Specifically, each indentation can be formed from a portion of the tube wall that is located between a pair of axially adjacent slits in the wall. More specifically, each indentation protrudes radially inward toward the center of the tube to form a passageway that can be used to thread the deflection wire through the indentation. As intended for the present invention, a plurality of such indentations can be formed in an axial direction along the tube to concertedly hold the deflection wire.

For some applications, in addition to creating a planar hoop in the distal portion of the catheter as discussed above, the catheter can also use the proximal portion for creating a gentle curve that will move the hoop relative to the longitudinal axis of the catheter. For this purpose, a tube with slits is also provided. The centerlines for slits of the proximal section, however, are azimuthally displaced from the centerlines of distal section slits by approximately ninety degrees. Further, if desired, the deflection system can also incorporate a bi-directional section that is positioned proximal to the laser cut tube. In one embodiment, a second laser cut tube is used in the bi-directional section that can be activated by two bi-directional pull wires that are manipulated at the catheter handle.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
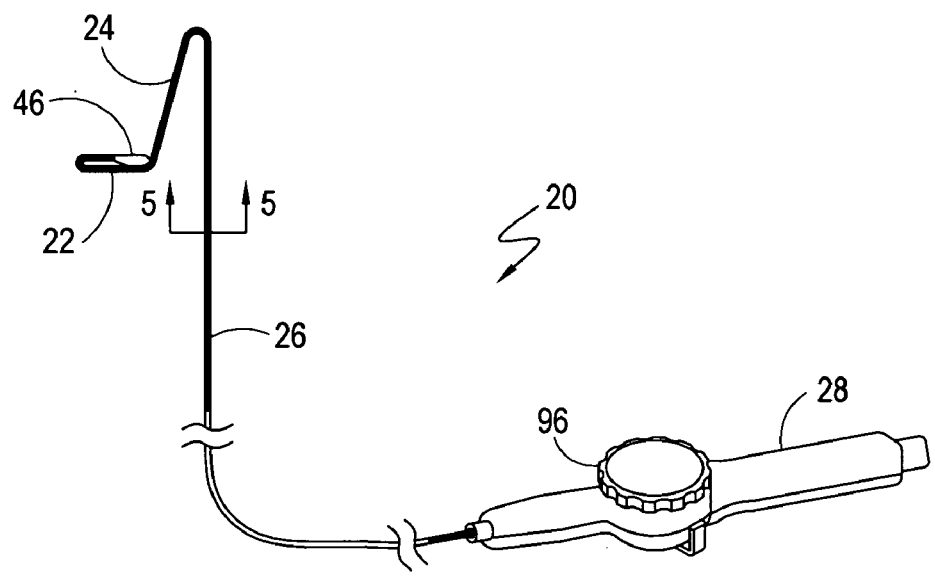
FIG. 1 is a perspective view of a cryo-catheter having a bi-directional control system and a system for deflecting a section of the cryo-catheter into a hoop configuration.

Referring initially to FIG. 1, a cryo-catheter for cryoablating a lesion in a body conduit of a patient is shown and generally designated 20. As indicated in FIG. 1, the cryo-catheter 20 can be manipulated into different configurations and orientations. To do this, the cryo-catheter 20 includes a system for deflecting a section 22 of the cryo-catheter 20 into a hoop configuration, as shown. It also includes a bi-directional control system for deflecting a section 24 of the cryo-catheter 20 in both a first direction and a second direction that is substantially coplanar and opposite the first direction. FIG. 1 further shows that the cryo-catheter 20 includes an elongated catheter body 26 that extends distally from a catheter handle 28. Although these deflecting systems are shown and disclosed herein as being part of a cryo-catheter 20, those skilled in the pertinent art will appreciate that these systems can be used as well in other types of catheters where bi-directional control or an actively produced hoop shaped configuration are desirable.

Figure 2:
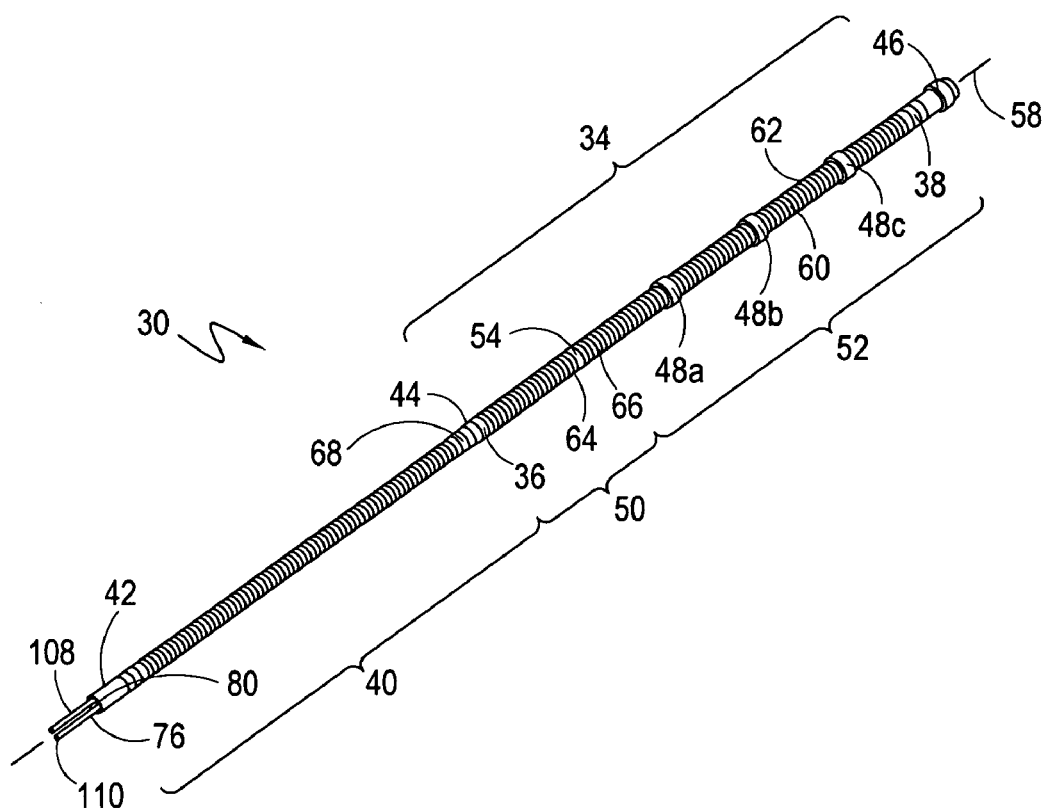
FIG. 2 is a perspective view of a distal portion of the cryo-catheter, shown with the flexible catheter jacket removed to reveal the internal structure of the catheter.

Referring now to FIG. 2, a distal portion of the cryo-catheter 20, generally designated 30, is shown with the outer catheter body 26 removed to reveal internal components. As shown, the cryo-catheter 20 includes a distal tube 34 having a proximal end 36 and a distal end 38, a proximal tube 40 having a proximal end 42 and a distal end 44, and a cryo-tip 46 that is mounted on the distal tube 34 at its distal end 38. For the embodiment shown, the cryo-catheter 20 also includes three EKG band electrodes 48a-c. FIG. 2 further shows that the distal tube 34 includes two distinct sections 50, 52, with section 50 extending from the proximal end 36 of the distal tube 34 to a section distal end 54 and section 52 extending from the distal end 54 of section 50 to the distal end 38 of the distal tube 34.

Figure 3:
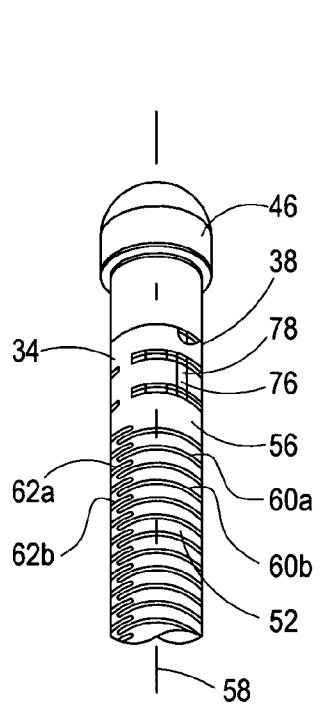
FIG. 3 is an enlarged, perspective view of the distal tip of the cryo-catheter.

Cross-referencing FIGS. 2 and 3, it can be seen that the distal tube 34 has a wall 56 and defines a tube axis 58. Section 52 of the distal tube 34 further includes a plurality of first slits, of which exemplary first slits 60a,b have been labeled, which are cut through the wall 56 and oriented in respective planes that are substantially perpendicular to the tube axis 58. As further shown, each first slit 60a,b extends azimuthally in an arc partway around the axis 58 and each has a center and a substantially same arc length, which is typically slightly greater than one-hundred eighty degrees. Further, it can be seen that the respective centers of these first slits 60 are aligned with each other in a first centerline that is oriented substantially parallel to the tube axis 58. For the embodiment shown, section 52 of the distal tube 34 is also formed with a plurality of second slits, of which exemplary second slits 62a,b have been labeled, and which, like the first slits 60a,b, establish a second centerline that is substantially parallel to the tube axis 58. Typically, the second slits 62a,b are cut into the tube wall 56 such that the second centerline is diametrically opposed to the first centerline (i.e. located one-hundred eighty degrees around the circumference of the distal tube 34 from the first centerline). With this arrangement of first slits 60 and second slits 62, the section 52 of the distal tube 34 can be transformed between a first, relaxed configuration wherein section 52 is substantially cylindrical shaped (as shown in FIGS. 2 and 3) and a second, deflected configuration wherein section 52 of the distal tube 34 is substantially hoop shaped (hoop shown in FIG. 1). For the cryo-catheter 20, the distal tube 34 is typically made of a thin walled stainless steel material (e.g. 304 alloy) that has been cut with a laser to form the slits 60, 62 described above. A more detailed description of the tube 34 can be found in co-pending, co-owned U.S. patent application Ser. No. 10/774,665, filed Feb. 9, 2004, which is hereby incorporated by reference in its entirety herein.

Continuing with FIGS. 2 and 3, the wall 56 of the distal tube 34 within the section 50 is formed with a plurality of first slits 64 and a plurality of second slits 66 which are cut through the wall 56 and oriented in respective planes that are substantially perpendicular to the tube axis 58. As further shown, each slit 64, 66 extends azimuthally in an arc partway around the tube axis 58 and each has a center and a substantially same arc length, which is typically slightly greater than one-hundred eighty degrees. Further, the respective centers of the first slits 64 are aligned with each other in a first centerline, the respective centers of the second slits 66 are aligned with each other in a second centerline and both first and second centerlines are oriented substantially parallel to the tube axis 58. For the section 50, the second centerline is diametrically opposed to the first centerline.

FIG. 2 further shows that the first slits 64 of section 50 are azimuthally displaced from the first slits 60 of section 52 by approximately ninety degrees. Thus, the first centerline of section 50 is azimuthally displaced from the first centerline of section 52 by approximately ninety degrees. Similarly, the second slits 66 of section 50 are azimuthally displaced from the second slits 62 of section 52 by approximately ninety degrees. With this arrangement of first slits 64 and second slits 66, the section 50 of the distal tube 34 can be transformed between a first, relaxed configuration wherein section 50 is substantially cylindrical shaped (as shown in FIGS. 2 and 3) and a second, deflected configuration wherein section 50 of the distal tube 34 is curved to establish a transition section between the hoop and the bi-directional section (see FIG. 1).

FIG. 2 also shows that the proximal tube 40 has a wall 68 and for the cryo-catheter 20, the proximal tube 40 is centered along the tube axis 58. Cross-referencing FIGS. 2 and 4 it can be seen that the wall 68 of the proximal tube 40 is formed with a plurality of first slits 70 and a plurality of second slits 72 which are cut through the wall 68 and oriented in respective planes that are substantially perpendicular to the tube axis 58. As further shown, each slit 70, 72 extends azimuthally in an arc partway around the tube axis 58 and each has a center and a substantially same arc length, which is typically slightly greater than one-hundred eighty degrees. Further, the respective centers of the first slits 70 are aligned with each other in a first centerline, the respective centers of the second slits 72 are aligned with each other in a second centerline and both first and second centerlines are oriented substantially parallel to the tube axis 58. For the proximal tube 40, the second centerline is diametrically opposed to the first centerline.

Figure 4:
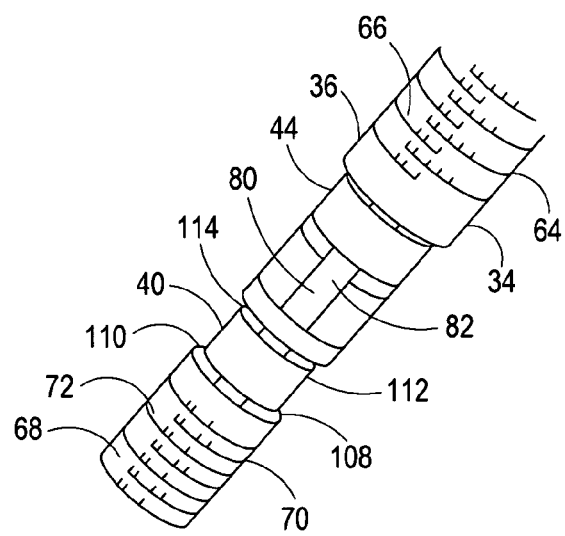
FIG. 4 is an enlarged, perspective view of the junction between the distal tube and the proximal tube of the catheter.

Continuing with cross-reference to FIGS. 2 and 4, it can be seen that the distal end 44 of the proximal tube 40 is attached to the proximal end 36 of the distal tube 34. As shown, the proximal tube 40 has a diameter that is slightly smaller than the diameter of the distal tube 34 allowing the distal end 44 of the proximal tube 40 to be inserted into the proximal end 36 of the distal tube 34 and attached thereto. Typically, the tubes 34, 40 are welded or bonded together. FIGS. 2 and 4 also show that the tube 34 is attached to the tube 40 with the centerline of the first slits 70 aligned with the center line of the first slits 64 of section 50 of the distal tube 34. Similarly, it can be seen that the tube 34 is attached to the tube 40 with the centerline of the second slits 72 aligned with the center line of the second slits 66 of section 50 of the distal tube 34.

Cross-referencing FIG. 1 with FIG. 3, it can be appreciated that the distal tube 34, proximal tube 40 and the proximal portion of the cryo-tip 46 are all disposed in the lumen 74 (see FIG. 5) of the distal portion of the catheter body 26. For the cryo-catheter 20, the distal portion of the catheter body 26 is made of a flexible, polymeric material which is bonded to the cryo-tip 46. On the other hand, the proximal portion of the catheter body 26 which extends from the handle 28 to the distal portion of the catheter body 26 is typically made of a polymeric material which is more rigid than the distal portion of the catheter body 26. For some implementations, the catheter body 26 within the hoop section 22 is made of a polymeric material filled with a conductive material to enhance the conductivity of the catheter body 26 in the hoop section 22. For example, the composite material typically includes between approximately ten weight percent and thirty weight percent (10 wt. %-30 wt. %) of filler material with the balance being polymeric matrix material. Suitable filler materials can include, but are not limited to, metals, metal alloys, ceramics, carbon and combinations thereof.

To deflect the section 22 (see FIG. 1) into a hoop shaped configuration, the cryo-catheter 20 includes a deflection wire 76 (see FIG. 5) having a distal end 78 that is attached to the distal end 38 of the distal tube 34, as shown in FIG. 3. For some embodiments (not shown), the distal end 78 of the deflection wire 76 is attached to the cryo-tip 46 instead of the distal end 38 of the distal tube 34. As further shown in FIG. 3, the attachment can be accomplished by indenting a portion of the distal tube 34 to create a nest between two axially adjacent slits 60 and then bonding or welding the wire 76 to the nest. As best appreciated with cross-reference to FIGS. 3 and 4, a central portion of the wire 76 is located within a sheath spring 80 (see also FIG. 6) having a distal end 82 which is attached to the proximal tube 40 near its distal end 44. As further shown in FIG. 4, the attachment is accomplished by indenting a portion of the proximal tube 40 and then bonding or welding the sheath spring 80 to the indented portion of the proximal tube 40.

Figure 7:
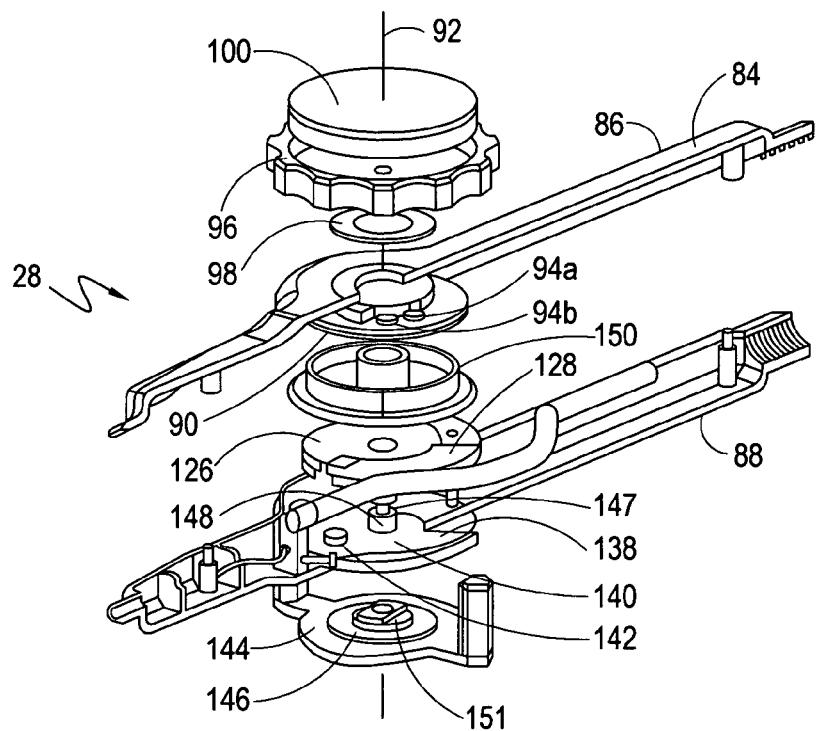
FIG. 7 is an exploded, perspective view of the catheter handle shown in FIG. 1.

From their respective distal ends 78, 82, the wire 76 and sheath spring 80 pass through the tubes 34, 40 and through the catheter body 26 (see also FIG. 5) to the handle 28 (see FIGS. 1 and 7). As shown in FIG. 7, the handle 28 includes a handle housing 84 having a handle top 86 and handle bottom 88. A generally disk shaped hoop reel 90 is positioned in and attached to the handle housing 84 to allow the hoop reel 90 to rotate about a rotation axis 92 relative to the housing 84. Although not shown, it is intended that the proximal end of the wire 76 will be partially wound around the hoop reel 90 and attached thereto using the attachment screws 94a,b. As shown, the screws 94a,b are located at a radial distance from the rotation axis 92. Also, the proximal end of the sheath spring 80 is attached to a ferrule (not shown) which is then fixedly attached to the handle top 86. With the above-described cooperation of structure, the hoop reel 90 can be rotated relative to the handle housing 84 to axially retract the deflection wire 76 and transform the distal tube 34. For purposes of the present invention, the wire 76 and hoop reel 90 cooperate to serve as a means for moving the wire 76 to a tensioned orientation.

Continuing with FIG. 7, it can be seen that the handle 28 includes a user operable knob 96, a friction washer 98 and a cosmetic cover 100 that are each positioned outside the handle housing 84 and centered on the rotation axis 92. As shown, the friction washer 98 is interposed between the handle top 86 and the knob 96. A screw (not shown) is provided to clamp the knob 96 toward the hoop reel 90 at a preselected clamping pressure. As a consequence, the friction washer 98 and the wall of the handle top 86 are sandwiched between the knob 96 and reel 90. With this structural arrangement, the user operable knob 96 can be rotated to selectively pull or release the deflection wire 76 (see FIG. 3), while the friction washer 98 holds the knob 96 in place after a preselected rotation. This allows the operator to release the knob 96 while maintaining a preselected deflection in the section 22 (see FIG. 1). For purposes of the present invention, the handle top 86, reel 90, knob 96 and friction washer 98 provide a means for locking the deflection wire in the tensioned orientation.

Figure 8:
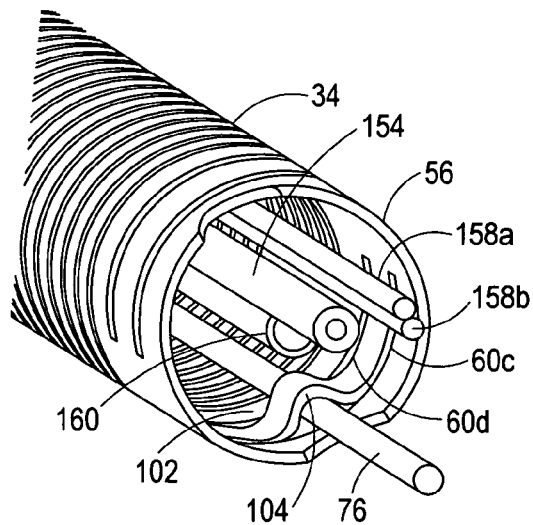
FIG. 8 is an enlarged, perspective view showing a section through the distal tube to illustrate an indentation for guiding a deflection wire.

Referring now to FIG. 8, it can be seen that within the distal tube 34, a guiding mechanism is provided to maintain the deflection wire 76 along the inner wall 102 of the distal tube 34 during axial retraction of the deflection wire 76. Specifically, as illustrated in FIG. 8, a plurality of indentations, such as indentation 104 shown, can be formed in the laser cut distal tube 34 to establish the guiding mechanism. Specifically, as shown, each indentation 104 can be formed in the wall 56 between a pair of axially adjacent slits, such as first slits 60c and 60d. Also shown, each indentation 104 forms a passageway that can be used to thread the deflection wire 76 though the indentation 104 to allow axial movement of the wire 76 relative to the indentation 104. In a typical embodiment of the cryo-catheter 20, approximately 5-15 axially spaced indentations 104 are used to maintain the deflection wire 76 along the inner wall 102 of the distal tube 34.

Figures 9A, 9B, 9C, 9D, 9E:
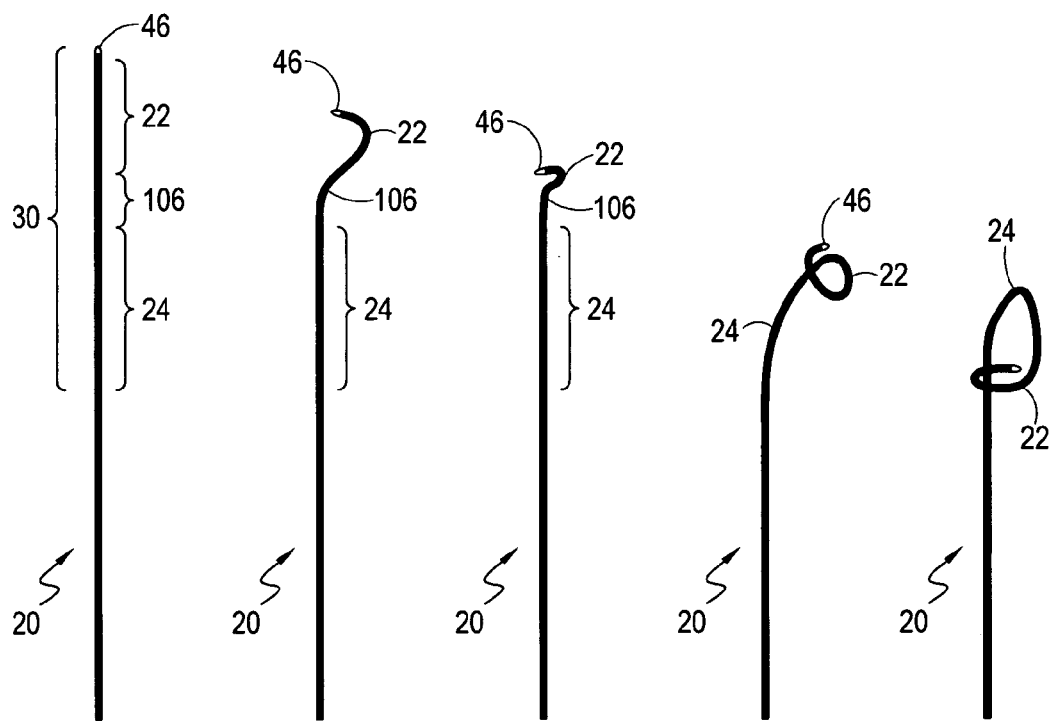
FIGS. 9A-E are a series of perspective views showing a distal portion of the cryo-catheter in various states of deflection.

The deflection of section 22 of the cryo-catheter 20 can best be appreciated with initial reference to FIG. 9A which shows the hoop section 22, bi-directional section 24 and transition section 106, all in a relaxed, undeflected state. FIG. 9B shows the cryo-catheter 20 after an initial retraction of the deflection wire 76. Comparing FIG. 9B with FIG. 9A, it can be seen that the initial retraction of the deflection wire 76 imparts a curvature to the hoop section 22 and the transition section 106. As shown in FIG. 9C, further retraction of the deflection wire 76 configures section 22 of the cryo-catheter 20 into a planar, hoop shaped configuration and imparts a curvature to the transition section 106. As best seen in FIG. 9C, the transition section 106 and the hoop section 22 deflect in different planes.

Figure 6:
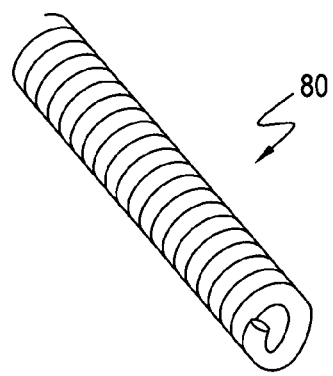
FIG. 6 is an enlarged, perspective view of a sheath spring.
Figure 10:
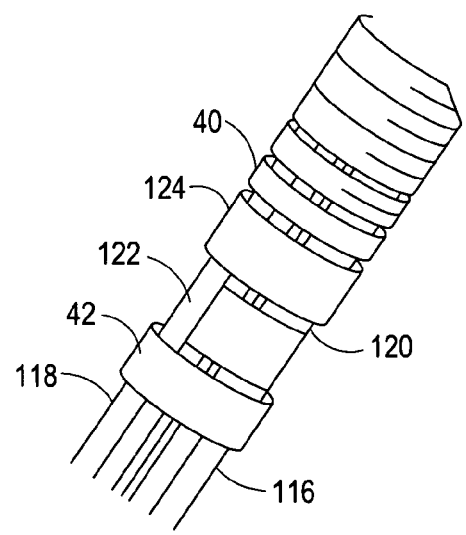
FIG. 10 is an enlarged, perspective view of the proximal end of the proximal tube.

To deflect the bi-directional section 24 (see FIG. 1), the cryo-catheter 20 includes pull wires 108, 110 having respective distal ends 112, 114 that are each attached to the proximal tube 40 near the distal end 44 of the proximal tube 40, as shown in FIG. 4. As further shown, the attachment points are located approximately one hundred eighty degrees apart around the circumference of the proximal tube 40. Also shown in FIG. 4, the attachment is accomplished by indenting a portion of the proximal tube 40 to create a nest between two axially adjacent slits and then bonding or welding the pull wires 108, 110 to the nest. As best appreciated with cross-reference to FIGS. 4 and 10, a central portion of each pull wire 108, 110 is located within a respective sheath spring 116, 118 (see also FIG. 6) having a respective distal end 120, 122 which is attached to the proximal tube 40 near its proximal end 42. As further shown in FIG. 10, the attachment is accomplished by indenting portions of the proximal tube 40 and then bonding or welding the respective sheath springs 116, 118 to the indented portion of the proximal tube 40. Note also from FIG. 10 that a portion of the proximal tube 40 distal to the nest can be slightly indented to form a distal abutment 124 for the sheath spring 118. For simplicity, sheath springs 80, 116 and 118 have been shown as simple tubes in FIGS. 4 and 10 and the actual helical structure of an exemplary sheath spring 80 is shown in FIG. 6.

From their respective distal ends 112, 114, 120, 122, the pull wires 108, 110 and sheath springs 116, 118 pass through the proximal tube 40 and through the catheter body 26 (see also FIG. 5) to the handle 28 (see FIGS. 1 and 7). A guiding mechanism can be provided to maintain each pull wire 108, 110 along the inner wall of the proximal tube 40 during an axial retraction of one of the pull wires 108, 110. Specifically, the guiding mechanism can be similar to the guiding mechanism described above for guiding the deflection wire 76 within the distal tube 34, as illustrated in FIG. 8. More specifically, a plurality of indentations can be formed in the laser cut proximal tube 40 to establish the guiding mechanism.

Figure 11A:
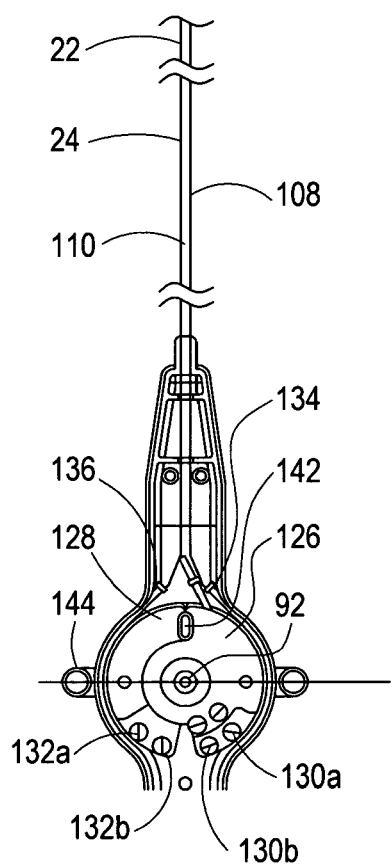
FIGS. 11A-E are a series of top plan views of the catheter handle (with the handle top removed) showing the bi-directional section of the catheter in various states of deflection.

As shown in FIG. 7, the handle 28 includes a clockwise (CW) reel 126 and a counter-clockwise (CCW) reel 128 that are positioned in and attached to the handle housing 84 to allow the reels 126, 128 to rotate about the rotation axis 92 relative to the housing 84. Although it is not shown in FIG. 7, it is to be appreciated that in use, the proximal end of the pull wire 108 is partially wound around the CW reel 126 and attached thereto using the attachment screws 130a,b (see FIG. 11A). Similarly, it is to be appreciated that the proximal end of the pull wire 110 will be partially wound around the CCW reel 128 and attached thereto using the attachment screws 132a,b (see FIG. 11A). As best seen in FIG. 11A, the screws 130a,b and 132a,b are each located at a radial distance from the rotation axis 92. For the cryo-catheter 20, the proximal end of sheath spring 116 is attached to a ferrule 134 which is then fixedly attached to the handle bottom 88. Similarly, the proximal end of sheath spring 118 is attached to a ferrule 136 which is then fixedly attached to the handle bottom 88. With this arrangement, the CW reel 126 can be rotated clockwise about the rotation axis 92 to selectively pull the pull wire 108 and the CCW reel 128 can be rotated counter-clockwise about the rotation axis 92 to selectively pull the pull wire 110.

As further shown in FIG. 7, the handle 28 includes a drive cog 138 having a drive wheel 140 that is formed with a protruding cog 142. As shown, the drive cog 138 is positioned in and attached to handle housing 84 for rotation about the rotation axis 92. Cross-referencing FIGS. 7 and 11A, it can be seen that when the cog 142 is rotated in a clockwise rotation direction it engages and rotates the CW reel 126 and when the cog 142 is rotated in the counter-clockwise rotation direction it engages and rotates the CCW reel 128. FIG. 7 further shows that each reel 126, 128 and the drive wheel 140 are stacked along the rotation axis 92 and positioned inside the handle housing 84 opposite a user operable turn knob 144 that is positioned outside the handle housing 84. A friction washer 146 is interposed between the handle bottom 88 and the knob 144. A screw 147 is then used to clamp the knob 144 toward the drive wheel 140 at a preselected clamping pressure. As a consequence, the friction washer 146 and the wall of the handle bottom 88 are sandwiched between the turn knob 144 and drive wheel 140. With this structural arrangement, the user operable turn knob 144 can be rotated to selectively retract either pull wire 108, 110, while the friction washer 146 "locks" the knob 144 in place after a preselected rotation. This allows the operator to release their hand from the knob 144 while maintaining a preselected tip deflection.

Continuing with FIG. 7, it can be seen that the drive cog 138 is formed with a spacer hub 148 to allow the reels 126, 128 to rotate after clamping the drive wheel 140 to the knob 144. In addition, a washer 150 is interposed between the reels 126, 128 and the hoop reel 90 to allow the hoop reel 90 to rotate independently of the reels 126, 128. A flat 151 formed on the knob 144 engages a corresponding flat (not shown) on the drive wheel 140 such that the knob 144 and drive wheel 140 rotate together.

Figure 11B:
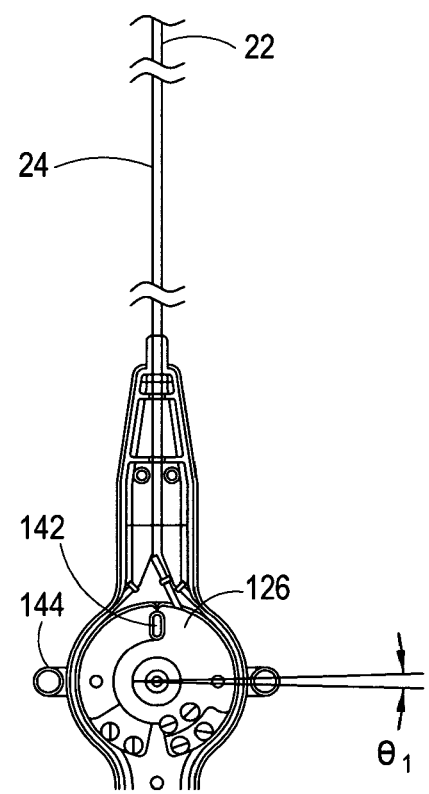

Operation of the bi-directional system for deflecting section 24 of the cryo-catheter 20 can best be appreciated with reference to FIGS. 11A-E. Beginning with FIG. 11A, the system is shown with the section 24 in the undeflected or neutral state. In this state, there is no applied tension to either pull wire 108,110. As further shown in FIG. 11A, in the neutral state, the cog 142 is positioned between the CW reel 126 and COW reel 128 with a gap between the cog 142 and reels 126,128. Thus, as best seen in FIG. 11B, the user operable knob 144 must be rotated through a small angle, $\theta_1$, before the cog 142 contacts and engages the CW reel 126. The functionality of the gap will be described in greater detail below. For purposes of the present invention, the pull wires 108, 110, cop 142, CW reel 126, CCW reel 128, and user operable knob 144 cooperate to serve as a means for selectively tensioning the first pull wire 108 and the second null wire 110. Further, the relationship between the cop 142, the pap and the reels 126, 128 provides a means for delaying an application of tension to said first pull wire 108 until tension in said second pull wire 110 has been released.

Figure 11C:
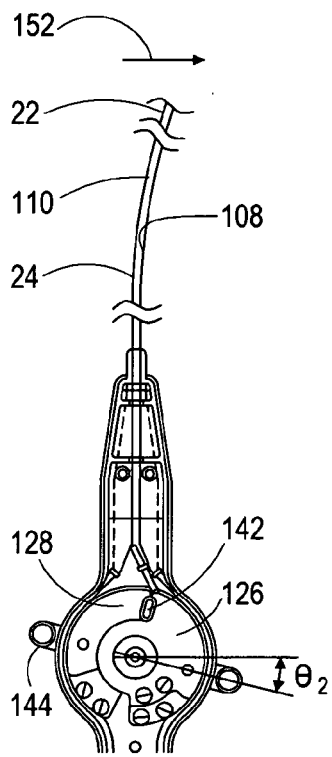

FIG. 11C shows the cryo-catheter 20 after a rotation of user operable knob 144 through an angle, $\theta_2$. It can be seen by comparing FIG. 11C with FIG. 11B that rotation of the knob 144 through an angle, $\theta_2$, causes the knob 144 to engage the CW reel 126 and rotate the CW reel 126 in a clockwise direction. This action, in turn, retracts the pull wire 108 and deflects section 24 of the cryo-catheter 20 in a first direction as indicated by arrow 152, as shown. The deflection of the section 24 pulls the pull wire 110 distally, which in turn rotates the CCW reel 128 clockwise as shown. However, it can be seen from FIG. 11C that a gap is still present between the cog 142 and the CCW reel 128.

Figure 11D:
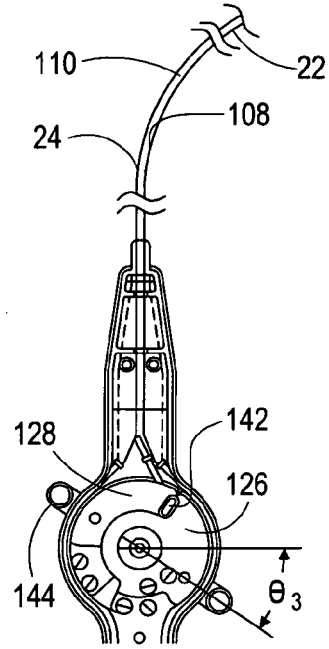

FIG. 11D shows the cryo-catheter 20 after a rotation of user operable knob 144 through an angle, $\theta_3$. This action, in turn, causes a further rotation of the CW reel 126 in a clockwise direction, further retracts the pull wire 108 and deflects section 24 of the cryo-catheter 20 to a greater extent. The increased deflection of the section 24 pulls the pull wire 110 distally, which in turn rotates the CCW reel 128 clockwise as shown. However, the initial gap (see FIG. 11A) is sized large enough so that the clockwise rotation of the CCW reel 128, due to the pull wire 110, does not cause the CCW reel 128 to engage and rotate the cog 142.

Figure 11E:
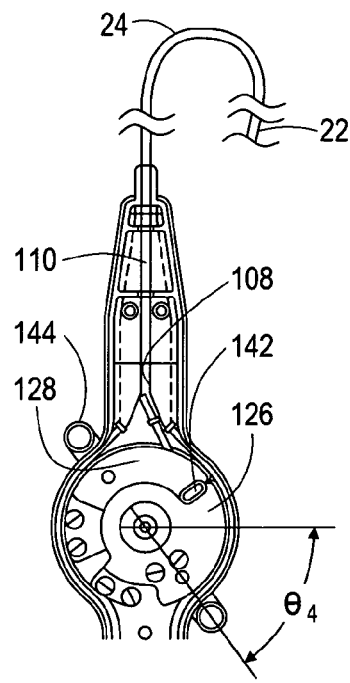

FIG. 11E shows the cryo-catheter 20 after a rotation of user operable knob 144 through an angle, $\theta_4$, that is equal to approximately forty-five degrees. This rotation of the knob 144 results in a deflection of the section 24 that is approximately equal to one hundred-eighty degrees, as shown. FIG. 11E further shows that a gap is present between the cog 142 and the CCW reel 128. From the above description, it is apparent that the CCW reel 128 does not engage or apply a force on the cog 142 during a rotation of the knob 144 from the neutral position (FIG. 11A) to the position shown in FIG. 11E. It follows that when the knob 144 is rotated counterclockwise from the position shown in FIG. 11E to the neutral position (FIG. 11A) that the cog 142 does not engage the CCW reel 128. Specifically, due to the gap between the cog 142 and reels 126, 128, the pull wire 110 is not pulled distally by the CCW reel 128 as the tension in the pull wire 108 is released. This allows the section 24 to smoothly recover from large deflections such as the large deflection shown in FIG. 11E. Moreover, FIG. 11A shows that the bi-directional system of the cryo-catheter 20 is functionally symmetric and accordingly it can be expected that a counterclockwise rotation of the cog 142 will result in a deflection of the section 24 in a direction opposite to arrow 152 shown in FIG. 11C.

The deflection of bi-directional section 22 can also be appreciated with reference to FIGS. 9C-9E and FIG. 1. Beginning with FIG. 9C, the cryo-catheter 20 is shown with the hoop section 22 and transition section 106 deflected and the bi-directional section 22 in a relaxed, undeflected state. FIG. 9D shows the cryo-catheter 20 after an initial retraction of the pull wire 108 (see also FIG. 11D). As shown in FIG. 9E, further retraction of the pull wire 108 results in a deflection of the section 24 that is approximately equal to one hundred-eighty degrees, in a first direction as indicated by arrow 152. FIG. 1 shows the bi-directional section after the pull wire 108 has been released and the pull wire 110 has been pulled distally by the CCW reel 128. This transition from FIG. 11E to FIG. 1 is accomplished by moving the knob 144 counterclockwise approximately ninety degrees. Comparing FIGS. 11A-E to FIG. 1, it can be seen that the bi-directional section 24 in FIG. 1 has been deflected in a direction that is opposite and coplanar to the direction of arrow 152.

Figure 5:
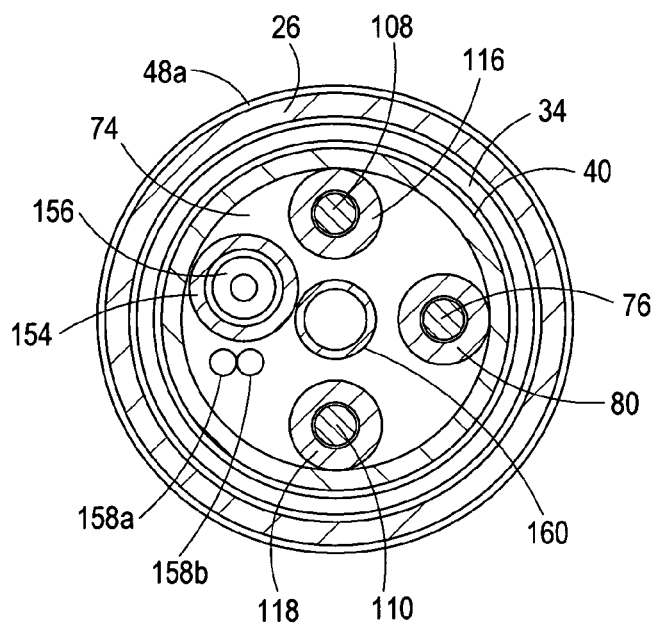
FIG. 5 is a cross-sectional view as seen along line 5-5 in FIG. 1, showing the distal portion of the cryo-catheter in a relaxed, undeflected state.

FIGS. 5 and 8 also show that the cryo-catheter 20 includes a refrigerant supply line having a supply tube 154 and a capillary tube 156, with the capillary tube 156 attached to the distal end of the supply tube 154. With this combination, an extracorporeally located refrigerant supply unit (not shown) can be activated to introduce a regulated flow of refrigerant into the supply tube 154 for subsequent flow through the capillary tube 156. From the capillary tube 156, the refrigerant expands into the cryo-tip 46 (FIG. 1), or if desired into the hoop section 22, or both, absorbing heat as it expands. A return line is provided to exhaust expanded refrigerant. For the embodiment shown, the return line is established in the volume between the supply line and catheter body 26. FIG. 8 also shows that thermocouple wires 158a,b are provided to measure a cryo-tip 46 temperature. A pressure monitoring line 160, which typically extends from the cryo-tip 46 to an extracorporeally located pressure gauge (not shown) is provided to measure a pressure within the cryo-tip 46.

In one application of the cryo-catheter 20, the cryo-tip 46, hoop section 22 and bi-directional section 24 are introduced into the left atrium through an introducer sheath (not shown) using a trans-septum approach. Once in the left atrium, section 22 is deflected into a hoop shape or partial hoop shape. Next, part or all of the deflected section 22 is placed into contact with target tissue which is typically peripheral tissue surrounding an ostium where a pulmonary vein connects with the left atrium. Deflection of the bi-directional section 24 can be used to achieve the desired contact between the hoop section 22 and the target tissue. Once adequate contact is made, refrigerant is expanded in the cryo-tip 46, hoop section 22 (or both) until an adequate lesion has been created. Sections 22, 24 of the cryo-catheter 20 can then be re-configured to contact other targeted tissue or removed from the vasculature to complete the procedure.

While the particular Active System for Deflecting a Distal Portion of a Catheter into a Hoop Configuration and corresponding methods of use and preparation as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A system for deflecting a distal portion of a catheter into a substantially hooped configuration, said system comprising:
    an elongated catheter body defining a longitudinal axis and having a proximal portion and a distal portion, with the distal portion being formed with a lumen;
    a tube disposed in said lumen and having a wall formed with a plurality of slits, said tube being transformable between a first, relaxed configuration wherein said tube is substantially cylindrical shaped and a second, deflected configuration wherein said tube is substantially hoop shaped;
    a deflection wire having a distal end attached to said tube and a proximal end, with said wire being threaded through adjacent slits to hold said wire against the wall of the tube; and
    a means operable on the proximal end of said deflection wire for moving said deflection wire axially to a tensioned orientation to transform said tube from the first configuration to the second configuration and reshape the distal portion of the catheter.

2. A system as recited in claim 1 further comprising a means for locking said deflection wire in the tensioned orientation.

3. A system as recited in claim 1 wherein said tube includes a plurality of indentations, with each indentation formed in said tube wall between a pair of axially adjacent slits, and wherein each indentation forms a passageway for threading said deflection wire therethrough.

4. A system as recited in claim 1 wherein said tube is made of a metal.

5. A system as recited in claim 1 further comprising a catheter handle having a handle housing and wherein said moving means comprises a reel attached to said housing for rotation relative to said housing about a rotation axis, with said proximal end of said deflection wire attached to said reel at a distance from said rotation axis.

6. A system as recited in claim 1 wherein said tube has a distal section for deflection within a first plane to establish a hoop and a proximal section for deflection in a second plane, said second plane being non-coplanar with said first plane.

7. A system as recited in claim 6 wherein said tube defines a tube axis; said distal tube section is formed with a plurality of first slits cut through the tube wall in respective planes substantially perpendicular to the tube axis, with each first slit extending azimuthally in an arc partway around the tube axis from a first end to a second end and defining a center midway therebetween, said centers of said first slits being aligned along a first centerline substantially parallel to the tube axis; and said proximal tube section is formed with a plurality of second slits cut through the tube wall in respective planes substantially perpendicular to the tube axis, with each second slit extending azimuthally in an arc partway around the axis from a first end to a second end and defining a center midway therebetween, and wherein the respective centers of the second slits are aligned along a second centerline that is substantially parallel to the tube axis and azimuthally displaced from the first centerline.

8. A system as recited in claim 7 wherein said second centerline is azimuthally displaced from the first line by approximately ninety degrees.

9. A system for reconfiguring and articulating a catheter while a portion of the catheter is positioned in a body conduit of a patient, said system comprising:
    an elongated catheter body having a distal portion and a proximal portion, with the catheter body being formed with a lumen;
    a tube disposed in said lumen and having a wall formed with a plurality of slits, said tube being transformable between a first, relaxed configuration wherein said tube is substantially cylindrical shaped and a second, deflected configuration wherein said tube is substantially hoop shaped;
    a means for deflecting said proximal portion in a first direction and in a second direction, wherein said first direction is coplanar and opposite to said second direction;
    a deflection wire attached to said tube, with said wire being threaded through adjacent slits to hold said wire against the wall of the tube; and
    a means operable on said deflection wire for moving said deflection wire to a tensioned orientation to transform said tube from the first configuration to the second configuration and reshape the distal portion of the catheter to form a hoop-shaped lesion during cryogenic treatment.

10. A system as recited in claim 9 further comprising a means for locking said deflection wire in the tensioned orientation.

11. A system as recited in claim 9 wherein said tube wall has an inner wall surface and a plurality of indentations, with each indentation formed in said tube wall between a pair of axially adjacent slits, and wherein each indentation forms a passageway for threading said deflection wire therethrough.

12. A system as recited in claim 11 further comprising a catheter handle having a handle housing and wherein said moving means comprises a reel attached to said housing for rotation relative to said housing about a rotation axis, with said proximal end of said deflection wire attached to said reel at a distance from said rotation axis.

13. A system as recited in claim 9 wherein said elongated catheter body defines a longitudinal axis, and wherein said deflecting means comprises:
    a first deflection wire having an end attached to said tube;
    a second deflection wire having an end attached to said tube; and
    a means for selectively tensioning said first deflection wire to deflect said proximal catheter body portion in the first direction and selectively tensioning said second deflection wire to deflect said proximal catheter body portion in the second direction.

14. A system as recited in claim 13 wherein said tensioning means comprises a means for delaying an application of tension to said first deflection wire until tension in said second deflection wire has been released.

15. A system as recited in claim 14 further comprising a catheter handle having a handle housing and wherein said tensioning means comprises a first reel attached to said housing for rotation relative to said housing about a rotation axis in a first rotation direction to pull said first deflection wire and a second reel attached to said housing for rotation relative to said housing about the rotation axis in a second rotation direction to pull said second deflection wire, with said first rotation direction being opposite said second rotation direction.

* * * * *